(12) United States Patent
Qu et al.

(10) Patent No.: US 11,518,973 B2
(45) Date of Patent: Dec. 6, 2022

(54) DEVICE AND METHOD FOR AUTOMATED ANTIBIOTIC SUSCEPTIBILITY TESTING OF GRAM-NEGATIVE BACTERIA

(71) Applicant: Yellow Sea Fisheries Research Institute Chinese Academy Of Fishery Sciences, Shandong (CN)

(72) Inventors: Keming Qu, Beijing (CN); Xuzhi Zhang, Shandong (CN); Jun Zhao, Shandong (CN); Jufa Chen, Shandong (CN); Yan Zhang, Shandong (CN); Qiufen Li, Shandong (CN); Dongsheng Ding, Shandong (CN); Xiaochun Wang, Shandong (CN); Xiaoyu Jiang, Shandong (CN)

(73) Assignee: Yellow Sea Fisheries Research Institute Chinese Academy of Fishery Sciences, Shandong (CN)

( * ) Notice: Subject to any disclaimer, the term of this patent is extended or adjusted under 35 U.S.C. 154(b) by 36 days.

(21) Appl. No.: 16/638,419

(22) PCT Filed: Mar. 19, 2019

(86) PCT No.: PCT/CN2019/078706
§ 371 (c)(1),
(2) Date: Feb. 11, 2020

(87) PCT Pub. No.: WO2019/179433
PCT Pub. Date: Sep. 26, 2019

(65) Prior Publication Data
US 2021/0371802 A1    Dec. 2, 2021

(30) Foreign Application Priority Data
Mar. 19, 2018 (CN) .......................... 201810225890.4

(51) Int. Cl.
*C12Q 1/18* (2006.01)
*C12M 1/34* (2006.01)
*C12M 1/00* (2006.01)
*G01N 33/543* (2006.01)
*G01N 33/569* (2006.01)
*G01N 15/06* (2006.01)

(52) U.S. Cl.
CPC ............ *C12M 41/36* (2013.01); *C12M 29/04* (2013.01); *C12M 41/12* (2013.01); *C12Q 1/18* (2013.01); *G01N 15/0656* (2013.01); *G01N 33/5438* (2013.01); *G01N 33/56911* (2013.01)

(58) Field of Classification Search
CPC .......... C12M 41/36; C12M 41/12; C12Q 1/18; G01N 15/0656; G01N 33/5438
See application file for complete search history.

(56) References Cited

U.S. PATENT DOCUMENTS

| 10,214,763 B2 | 2/2019 | Ekinci |
| 2005/0142537 A1 | 6/2005 | Rieder |
| 2017/0044589 A1 | 2/2017 | Johnson |

FOREIGN PATENT DOCUMENTS

| CN | 101339153 A | 1/2009 |
| WO | WO 2019/179433 A1 | 9/2019 |

OTHER PUBLICATIONS

Tan et al. 1998 (A rapid method for determination of in vitro susceptibility to antibiotics with a bulk acoustic wave bacterial growth biosensor; Letters in Applied Microbiology 27: 57-61). (Year: 1998).*
International Search Report and Written Opinion in International Application No. PCT/CN2019/078706, dated Sep. 26, 2019 (7 pages).

* cited by examiner

*Primary Examiner* — Mary Maille Lyons
(74) *Attorney, Agent, or Firm* — Nixon Peabody LLP

(57) ABSTRACT

An antibiotic susceptibility testing device of gram-negative bacteria, as well as a corresponding method, are discussed. The device has a temperature control unit (including a constant temperature chamber) and a contactless conductivity-based measurement system. Disposable glassy or PVC tubes are used as test vessels for AST. In the performance of AST assay, appropriate kind of liquid medium containing identical amount of target bacterial cells and target antibiotics at different concentrations are loaded into test tubes, following by incubation in the device at a setup temperature. The bacterial growth profile is monitored by collecting the differential values ($\Delta C$) of conductivity of liquid medium, which depend on the proliferation of viable cells. Outcome of $\Delta C$ indicates whether the target bacterial cells are completely inhibited by the test antibiotic or not, enabling the user to judge the value of the minimal inhibitory concentration (MIC) simply.

4 Claims, 2 Drawing Sheets

DEVICE AND METHOD FOR AUTOMATED ANTIBIOTIC SUSCEPTIBILITY TESTING OF GRAM-NEGATIVE BACTERIA

CROSS-REFERENCE TO RELATED APPLICATIONS

This application is a U.S. national stage of PCT/CN2019/078706 filed Mar. 19, 2019, which claims priority to and the benefit of Chinese Patent Application No. 201810225890.4, filed Mar. 18, 2018, all the contents of which are incorporated herein by reference in their entireties.

FIELD

The present invention relates to a measurement technique for evaluating the efficiency of antibiotics against bacteria, and more specifically antibiotic susceptibility testing (AST) of gram-negative bacteria.

BACKGROUND

*Escherichia coli, Proteus*, Dysentery *bacillus, Salmonella*, etc., are the most concerned gram-negative pathogenic bacteria, and can cause diarrhea and other infections. Thus they threat the health of human beings and breeding creatures. The employment of antibiotics is of a great milestone for human to battle against pathogenic bacteria. In order to guarantee appropriate prescriptions, AST of the involved bacteria should be conducted at early stage of the infection. Meanwhile, monitoring the drug-resistance of pathogenic bacteria and understanding the law of resistant trends are greatly meaningful for empirical prescriptions, and also is helpful to impede the emergence of drug-resistant strains caused by misuse or overuse of antibiotics.

AST is used to determine the concentration of antibiotics that is required to inhibit proliferation of target microorganism in vitro. Currently, disk diffusion, broth dilution and E test methods are popular in routine AST. Disk diffusion method is based on the principle that antibiotic-impregnated disk, placed on paper or agar previously inoculated with the test bacterium, pick-up moisture and the antibiotic diffuse radially outward through the medium producing an antibiotic concentration gradient. The concentration of the antibiotic at the edge of the disk is high and gradually diminishes as the distance from the disk increases to a point where it is no longer inhibitory for the organism, which then grows freely. When broth dilution and E test methods are employed, data of susceptibility are obtained according to bacterial proliferation or not in the presence of antibiotics at different concentrations. All of these methods are time-consuming. Generally, they will take more than one week. This issue, namely the slow response, challenges their applications in clinical case, where fast response is of great significance in order to conduct timely treatment. Recently, based on modern molecular techniques (e.g. polymerase chain reaction, gene chip, whole-genome sequencing) some fast approaches have been reported frequently. Though the assay time reduces apparently, these emerging methods are still laborious and cost. In addition, they cannot directly report the minimal inhibitory concentration (MIC). By contrast, another alternative approach, which is based on on-line monitoring bacterial growth with automated optical measurement system (e.g. BACTEC-TB460 and BACTEC960), is superior to that employing molecular techniques in simplicity and efficiency. However, these automated systems, as well as involved auxiliary materials and regents, are expensive. These disadvantages challenge its wide-spread application.

SUMMARY

The present invention provides an automated device, as well as a relevant method, for AST of gram-negative bacteria.

The structure and working principle of this invention are as following: The device comprises a temperature control unit. In the box-shape temperature control unit, a row or a few rows of test channels are arranged vertically. Each test channel includes an actuator electrode A, a pick-up electrode L and a pick-up electrode S. These three copper cylinder electrodes are coaxially fixed with fixing plate at a desired distance, respectively. One-end-closed disposable glassy or PVC tubes are used as test vessels for AST. These test tubes are installed into the temperature control unit through holes in the unit cover, consequently crossing the actuator electrode A, the pick-up electrode L and the pick-up electrode S in turn. These holes in the unit cover are coaxially above the test channels. Nozzle of the test tube is stuffed with a disposable syringe filter to keep away undesired microbes from air. In the temperature control unit, temperature can be adjusted to a desired degree over the range of 0~70° C. The nonidentity of temperature in the unit is within 0.5° C. All the components of the temperature control unit can be purchased in electronic component store, apart from those components formed the test channels.

A certain amount of liquid medium containing target gram-negative bacterial cells and target antibiotics is loaded in the disposable test tube. The test tube is inserted into the test channel. An AC voltage at high frequency is applied to the actuator electrode, forming composite capacitances via the air between test tube and electrode and the tube wall between the air and liquid medium, respectively. Meanwhile, an equivalent resistor RL is formed between the actuator electrode A and pick-up electrode L; an equivalent resistor RS is formed between the actuator electrode A and pick-up electrode S. Thus on the pick-up electrode L a first coupling signal of capacitance and resistor (C-Rc L) is present; and on the pick-up electrode S a second coupling signal of capacitance and resistor (C-Rc S) is present. The magnitude of the detected resistor signal is proportional to the concentration and mobility of the ionic charge carriers in the liquid medium, indicating the growth of target bacterial cells. All of rest response signals can impair the sensitivity and accuracy of the measurement. Therefore, in order to improve the sensitivity of differentiation of bacterial growth, the differential value ($\Delta C$) between C-Rc L and C-Rc S is recorded with a capacitively coupled contactless conductivity detector.

Furthermore, the device comprises a capacitively coupled contactless conductivity detector, which is controlled by a computer. The capacitively coupled contactless conductivity detector (ER815) is produced by eDAQ company (Australia), as well as the relevant TERA TERM software. The actuator electrode A, pick-up electrode L and pick-up electrode S are all linked to the capacitively coupled contactless conductivity detector.

Specifically, the actuator electrode A, pick-up electrode L and pick-up electrode S are all copper cylinders with 0.95 mm wall thickness. Their lengths are 16 mm, 16 mm and 10 mm, respectively. The copper cylinders are with an external diameter of 4.00 mm, and with an inner diameter of 3.05 mm.

According to the requirement of real test work conditions and the parameters of ER815 capacitively coupled contactless conductivity detector, the number of the test channel can be 1, 8, 16, 24, or 32. Namely, 1, 8, 16, 24, or 32 test channels can be arranged in the temperature control unit.

In some of the embodiments, the disposable test tube is in length of 12±2 cm, inner diameter of 2.60 mm, and outer diameter of 3.00 mm.

Preferably, 0.22 μm disposable syringe filter is selected.

Furthermore, a method for AST assay is provided in this invention, using as-proposed automated AST device above. Involved steps are listed as following:

a. Preparation of liquid medium containing desired bacterial cells;

b. Preparation of solution of target antibiotic;

c. Loading the liquid medium and antibiotic solution into a sterilized disposable test tube, following by stuffed the nozzle of the test tube with a disposable syringe filter;

d. Setting the parameters of the capacitively coupled contactless conductivity detector: excitation amplitude of 1000 V, excitation frequency of 1.6 MHz, collection period of conductivity value of 1 s and total collection times of 20,000~30,000;

e. Inserting the disposable test tube into a test channel and switching on the capacitively coupled contactless conductivity detector to collect the differential values (ΔCs) between the C-$R_c$ L and C-$R_c$ S;

f. Judging the bacterial cells proliferation result based on the ΔCs at the final point. The ΔC is equal to or larger than 10.0 μS/cm, indicating a proliferation; and ΔC is equal to or lower than 1.0 μS/cm, indicating a completely inhibition. The MIC is defined as the lowest concentration of antibiotic resulting in complete inhibition of growth.

Furthermore, if the ΔC is between 1.0 μS/cm and 10.0 μS/cm, repeating the test to exclude accidental error.

In one embodiment, the antibiotic solution is prepared with ultrapure water and antibiotic regent.

All of involved hardware, containers, tools and consumables need to be sterilized in the operation.

Liquid medium in each disposable test tube contains identical amount of target bacteria cells (2~5 colony-forming units, CFUs) for the same AST assay.

Furthermore, the gram-negative bacteria species includes *Helicobacter pylori, Escherichia coli, Proteus,* Dysentery bacillus, *Shigella, Pneumobacillus, Brucella, Influenzae, Parainfluenza, Yersinia, Catamycin, Acinetobacter, Legionella pneumophila, Bordetella pertussis, Bordetella pertussis, Pasteurella genus, Vibrio cholerae* and *Parahaemolyticus*.

Furthermore, the antibiotic species includes cefazolin, cefepime, cefotetan, ceftazidime, ceftriaxone, ciprofloxacin, gentamicin, levofloxacin, nitrofurantoin, cotrimoxazole, amoxicillin and clarithromycin. One or a few kinds of them can be tested in the same batch.

Furthermore, in the temperature control unit temperature can be adjusted to a desired degree over the range of 0~70° C. The nonidentity of temperature in the unit is within 0.5° C.

The time requirement for achieving an AST assay, namely the product of the collection period and total collection times, depends on not only the feature of the target bacteria but also the culture conditions. Generally, it is not larger than 12 hours.

Compared to traditional techniques, this invention is superior for conducting AST assays in a few fields, including:

(1) The structure of the device is simple and thus portable. It is an affordable instrument. Moreover, for the performance of test, neither optical regents nor auxiliary chemicals are needed. These enable cost-effective applications.

(2) Pretreatments for removing co-existing substances from tested samples are avoided because that the results obtained with this method are not affected by the presence of turbidity, astigmatism, etc.

(3) It is a full automatic operation, needing neither sample step in the assay process nor calculation step at the end of cultivation. These imply a simple and user-friendly tool.

BRIEF DESCRIPTION OF THE DRAWINGS

In order to more clearly illustrate the embodiments of the present invention, brief statement is provided here for the drawings. These drawings are aiming to help readers to understand some of the embodiments of the present invention. Whereas, technicians in this field can create more relevant drawings based on these drawings, rather than a creative contribution.

DETAILED DESCRIPTION

The assembly and application method of the present invention will be further stated below by means of embodiments. Apparently, the discussed embodiments are examples of the present invention, rather than all of the embodiments. Other embodiments obtained by technicians in this field without creative work are in the scope of protection.

Figure 1:
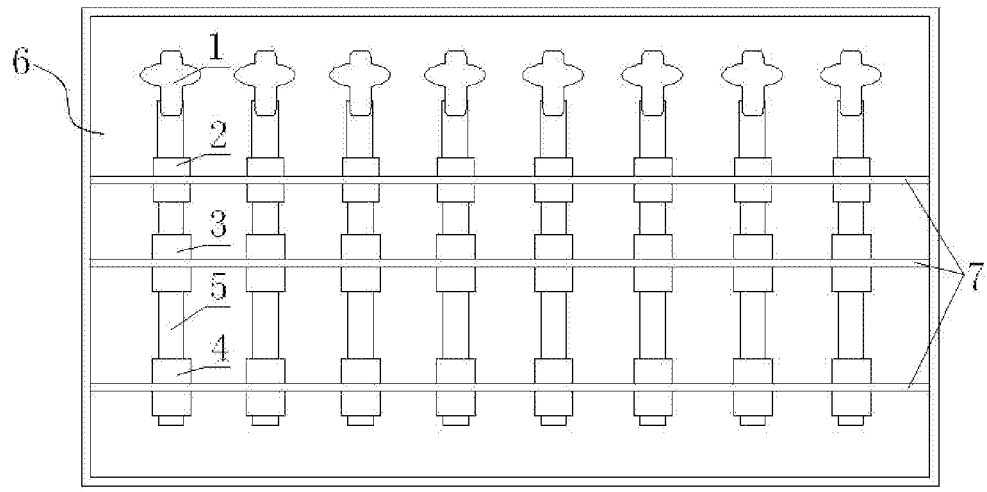
FIG. 1 schematically shows the structure of the device in accordance with an embodiment of the present invention, wherein 1: disposable syringe filter; 2: pick-up electrode L; 3: pick-up electrode S; 4: actuator electrode A; 5: disposable test tube; 6: constant temperature chamber; 7: fixing plate.

As shown in FIG. 1, an automated device for AST assay of gram-negative bacteria comprises a temperature control unit. There is a constant temperature chamber (6) in the temperature control unit. One or a row of test channels are arranged vertically in the constant temperature chamber (6). Each test channel has an actuator electrode A (4), a pick-up electrode L (2) and a pick-up electrode S (3). These three cylinder electrodes are coaxially fixed with fixing plate (7). One-end-closed disposable glassy or PVC tubes (5) are used as test vessels. These test tubes are installed into the temperature control unit through holes in the unit cover, consequently crossing actuator electrode A (4), pick-up electrode L (2) and pick-up electrode S (3) in turn. These holes in the unit cover are coaxially above the test channels. Nozzle of the test tube is stuffed with a disposable syringe filter (1). In the temperature control unit temperature can be adjusted to a desired degree over the range of 0~70° C. The nonidentity of temperature in the unit is within 0.5° C. All the components of the temperature control unit can be purchased in electronic component store, apart from those components formed the test channels.

Figure 2:
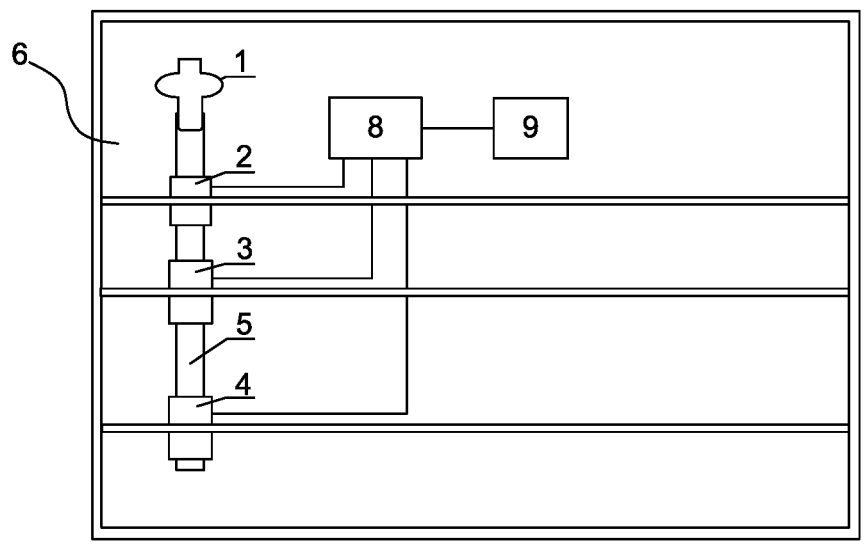
FIG. 2 schematically shows the struction of the device with a capacitively coupled contactless conductivity detector and a computer in accordance with an embodiment of the present invention.
Figure 3:
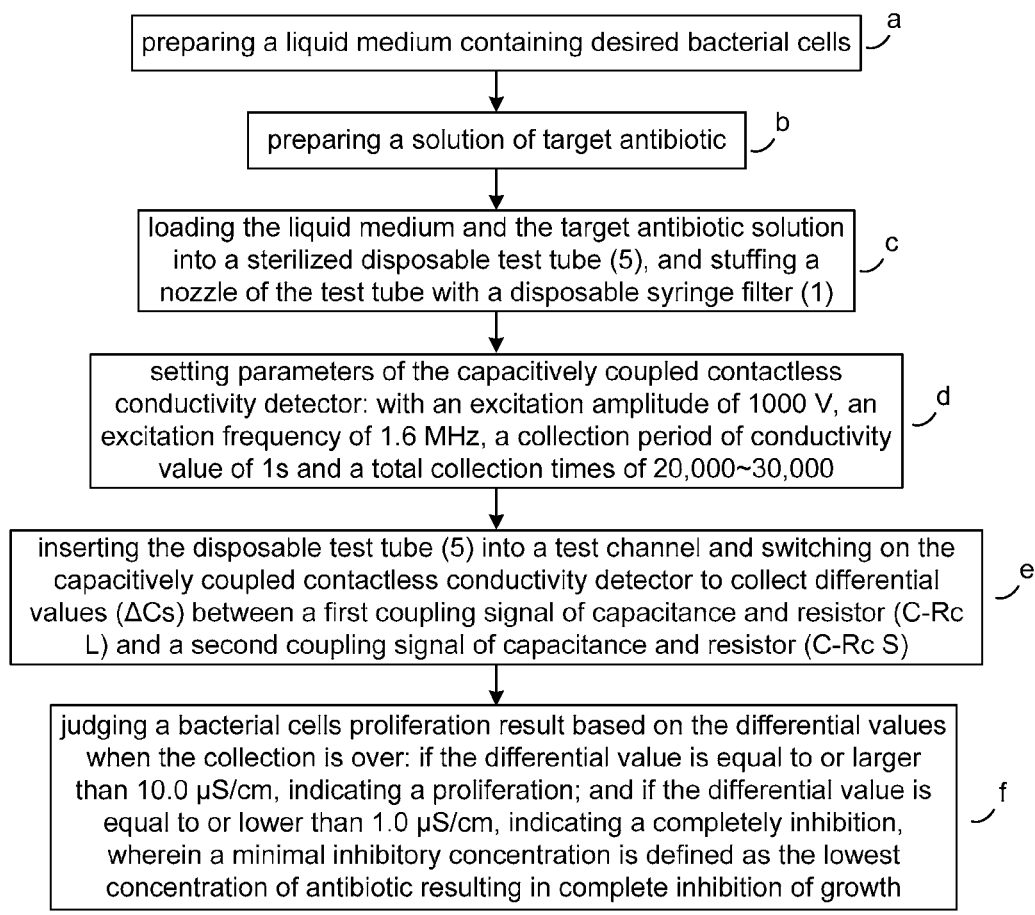
FIG. 3 schematically shows a flowchart of a method for AST of gram-negative bacteria.

Furthermore, the device comprises a capacitively coupled contactless conductivity detector (shown as label 8 in FIG. 2), which is controlled by a computer (shown as label 9 in FIG. 2). The capacitively coupled contactless conductivity detector (ER815) is produced by eDAQ company (Australia), as well as the relevant TERA TERM software. The actuator electrode A, pick-up electrode L and pick-up electrode S are all linked to the capacitively coupled contactless conductivity detector.

In one embodiment, the distance between the pick-up electrode L (2) and pick-up electrode S (3) is 5 mm; and the distance between the pick-up electrode S (3) and the actuator electrode A (4) is 10 mm. In every test channel the three electrodes are coaxially fixed with fixing plate (7).

Specifically, in one embodiment, the actuator electrode A (4), pick-up electrode L (2) and pick-up electrode S (3) are all copper cylinders in external diameter of 4.00 mm with 0.95 mm wall thickness. Their lengths are 16 mm, 16 mm and 10 mm, respectively.

In one embodiment, according to the requirement of real test work conditions and the parameters of ER815 capacitively coupled contactless conductivity detector, the number of the test channel can be 1, 8, 16, 24, or 32. Namely, 1, 8, 16, 24, or 32 test channels can be arranged in the temperature control unit.

In one embodiment, the disposable test tube (5) is in length of 12±2 cm, inner diameter of 2.60 mm, and outer diameter of 3.00 mm.

Preferably, 0.22 μm disposable syringe filter (1) is selected.

Example 1

AST Array of Levofloxacin Against Dysentery *Bacillus*

Step 1: According to FIG. 1, an automated device with eight test channels is set up. An HtPot50 dry incubator, which is produced by ABSON Scientific Instruments Co. (Hefei, China), is used as a temperature control unit. The used 0.22 μm disposable syringe filter is produced by Zhejiang Aijiren INC (Quzhou, China). The actuator electrode A, pick-up electrode L and pick-up electrode S are all copper cylinders in external diameter of 4.00 mm with 0.95 mm wall thickness. Their lengths are 16 mm, 16 mm and 10 mm, respectively. In every test channel the three electrodes are coaxially fixed with fixing plate. The distance between the pick-up electrode L and pick-up electrode S is 5 mm; and the distance between the pick-up electrode S and the actuator electrode A is 10 mm. All of the electrodes of the eight test channels are linked to an ER815 capacitively coupled contactless conductivity detector (eDAQ Ltd, Australia). The capacitively coupled contactless conductivity detector is controlled with TERA TERM software installed in E470c laptop computer (Legend Holdings Corporation, China).

Step 2: The temperature in the constant temperature chamber (6) is set to be 36° C. with a nonidentity ≤0.5° C. by clicking the button of temperature control.

Step 3: Involved hardware, containers, tools, consumables and special liquid medium for Enterobacteriaceae are sterilized with high temperature steam (121° C.), following by cooling down to room temperature in sterile vessels. In the special liquid medium the concentrations of beef powder, proteose peptone, lactose, No. 3 bile salt, sodium citrate, sodium thiosulfate and ferric citrate are 5.0, 5.0, 10.0, 8.5, 8.5, 8.5 and 1.0 g/L, respectively.

Step 4: A series of levofloxacin solutions at concentrations of 0.5, 1.0, 2.0, 4.0, 6.0, 8.0, 10.0 and 12.0 g/L are prepared with ultrapure sterile water.

Step 5: Eight milliliter sterilized special liquid medium for Enterobacteriaceae is transferred into a 10 ml centrifuge tube with a pipette.

Step 6: Sixteen well-definite bacterial colonies are transferred from inoculating dish, on which Enterobacteriaceae is cultured for 18-20 h, into the 10 ml centrifuge tube to prepare bacterial suspension.

Step 7: One-end-closed disposable glassy tubes in length of 12 cm are used as test tubes. Their inner diameter and outer diameter are 2.60 mm and of 3.00 mm, respectively. Pipetting 995 μl bacterial suspension and 5 μl levofloxacin solutions at different concetrations into each test tube (5) to make test samples. In the final test samples the concentration of the levofloxacin is 0.25, 0.50, 1.00, 2.00, 3.00, 4.00, 5.00 and 6.00 mg/1, respectively.

Step 8: A disposable syringe filter (1) is stuffed into the nozzle of every test tube (5).

Step 9: Starting the application software on the laptop computer loaded with TERA TERM to set the parameters of the capacitively coupled contactless conductivity detector: excitation amplitude of 1000 V, excitation frequency of 1.6 MHz, collection period of conductivity value of 1 s and total collection times of 21600.

Step 10: The 8 as-prepared test tubes loaded with test samples are inserted into 8 test channels, respectively. Switching on the capacitively coupled contactless conductivity detector to collect the differential values (ΔCs) between the C-$R_c$ L and C-$R_c$ S.

Step 11: At the end of incubation, the values of ΔC obtained from No. 1, No. 2 and No. 3 test tubes are equal to or larger than 18.0 μS/cm, indicating that in the liquid medium Enterobacteriaceae grow in the presence of levofloxacin at concentrations of 0.25, 0.50 and 1.00 mg/l. Whereas, the values of ΔC obtained from No. 4, No. 5, No. 6, No. 7 and No. 8 test tubes are not more than 1.0 μS/cm, indicating that the growth of Enterobacteriaceae is completely inhibited. Therefore, the MIC of this antibiotic against the resent Enterobacteriaceae strain is 2.00 mg/l.

Example 2

Characterization of the Synergetic Effect of Levofloxacin and Clarithromycin Against *Helicobacter pylori*

Step 1 and step 2 are the same as stated in EXAMPLE 1.

Step 3: Involved hardware, containers, tools, consumables and special liquid medium for *Helicobacter pylori* are sterilized with high temperature steam (121° C.), following by cooling down to room temperature in sterile vessels. The special liquid medium is purchased from Qingdao Hope Bio-Technology Co., Ltd (Qingdao, China).

Step 4: Levofloxacin solutions at concentrations of 0.2, 0.4, 0.6 and 0.8 g/l are prepared with ultrapure sterile water. Clarithromycin solutions at concentrations of 0.2, 0.4, 0.6 and 0.8 g/l are prepared with ethyl alcohol.

Step 5: Eight milliliter sterilized special liquid medium for *Helicobacter pylori* is transferred into a 10 ml centrifuge tube with a pipette.

Step 6: Twelve well-definite bacterial colonies are transferred from inoculating dish, on which *Helicobacter pylori* is cultured for 18-20 h, into the 10 ml centrifuge tube to prepare bacterial suspension.

Step 7: One-end-closed disposable PVC tubes in length of 12 cm are used as test tubes (5). Their inner diameter and outer diameter are 2.60 mm and of 3.00 mm, respectively. Pipetting 995 μl bacterial suspension and 5 μl levofloxacin solutions at different concentrations into No. 1, No. 2, No. 3 and No. 4 test tube (5) to make test samples. In these final test samples the concentration of the levofloxacin is 0.10, 0.20, 0.30, and 0.40 mg/l, respectively. Pipetting 990 μl bacterial suspension, 5 μl levofloxacin solutions and 5 μl clarithromycin solutions into No. 5, No. 6, No. 7 and No. 8 test tube (5) to make the other batch of test samples. In these four test samples the concentrations of the levofloxacin and clarithromycin are both at 0.10, 0.20, 0.30, and 0.40 mg/l, respectively.

Step 8: A disposable syringe filter (1) is stuffed into the nozzle of every test tube (5).

Step 9: Starting the application software on the laptop computer loaded with TERA TERM to set the parameters of the capacitively coupled contactless conductivity detector: excitation amplitude of 1000 V, excitation frequency of 1.6 MHz, collection period of conductivity value of 1 s and total collection times of 28800.

Step 10: The 8 as-prepared test tubes (5) loaded with test samples are inserted into 8 test channels, respectively. Switching on the capacitively coupled contactless conductivity detector to collect the differential values ($\Delta Cs$) between the C-$R_c$ L and C-$R_c$ S.

Step 11: At the end of incubation, the values of $\Delta C$ obtained from No. 1, No. 2, No. 3 and No. 4 test tubes are equal to or larger than 22.0 μS/cm, indicating that in the liquid medium *Helicobacter pylori* grow in the presence of levofloxacin at concentrations of 0.10, 0.20, 0.30, and 0.40 mg/l. The values of $\Delta C$ obtained from No. 5 and No. 6 test tubes are equal to or larger than 17.0 μS/cm, indicating that *Helicobacter pylori* still grow in the presence of 0.10 and 0.20 mg/l levofloxacin, even companying with the same amount of clarithromycin. Whereas, the values of $\Delta C$ obtained from No. 7 and No. 8 test tubes are not more than 1.0 μS/cm, indicating that the growth is completely inhibited. This implies that 0.30 mg/l levofloxacin together with 0.30 mg/l clarithromycin can inhibit the growth of *Helicobacter pylori*.

Step 12: The same disposable PVC tubes in length of 12 cm are used as test tubes (5). Pipetting 995 μl bacterial suspension and 5 μl clarithromycin solutions at different concentrations into No. 1, No. 2, No. 3 and No. 4 test tube (5) to make test samples. In these final test samples the concentration of the clarithromycin is 0.10, 0.20, 0.30, and 0.40 mg/l, respectively.

Step 13: A disposable syringe filter (1) is stuffed into the nozzle of every test tube (5) as stated in Step 8.

Step 14: With the same approaches as stated in Step 9 and Step 10, values of $\Delta Cs$ are obtained.

Step 15: At the end of incubation, the values of $\Delta C$ obtained from No. 1, No. 2, No. 3 and No. 4 test tubes are equal to or larger than 14.0 μS/cm, indicating that *Helicobacter pylori* grow in the presence of clarithromycin at concentrations of 0.10, 0.20, 0.30, and 0.40 mg/l.

Step 16: The data obtained in Step 11 and Step 15 enable the user to draw a conclusion that there is apparently synergetic effect of levofloxacin and clarithromycin against *Helicobacter pylori*. Neither 0.20 mg/l levofloxacin nor 0.20 mg/l clarithromycin can work alone.

It is to be understood that the above embodiments are just the preferable examples. The present invention is not limited to these embodiments. Any modification, equivalent replacement, or improvement under the spirit and principle of the present invention, are under the scope of the present invention.

The invention claimed is:

1. A method for antibiotic susceptibility testing (AST) of Gram-negative bacteria with a device having a temperature control unit, a plurality of sterilized disposable test tubes, and a plurality of disposable syringe filters, the method comprising:
    assembling a plurality of test channels vertically in the temperature control unit,
    each of the plurality of test channels including an actuator electrode, a first pick-up
    electrode and a second pick-up electrode, coaxially fixed with a fixing plate;
    preparing a liquid medium containing bacterial cells to be measured;
    preparing a solution of target antibiotic;
    loading the liquid medium and the target antibiotic solution into each of the plurality of sterilized disposable test tubes, and covering an opening of the test tube with a disposable syringe filter;
    setting parameters of a capacitive coupled contactless conductivity detector: with an excitation amplitude of 1000 V, an excitation frequency of 1.6 MHz, a collection period of conductivity value of 1s and total collection times of 20,000 to 30,000; and
    respectively inserting the plurality of sterilized disposable test tubes into each of the plurality of test channels and switching on the capacitive coupled contactless conductivity detector to collect differential values ($\Delta Cs$) between a first coupling signal of capacitance and resistor (C-Rc L) and a second coupling signal of capacitance and resistor (C-Rc S).

2. The method for AST according to claim 1, wherein the Gram-negative bacteria species includes *Helicobacter pylori, Escherichia coli, Shigella, Pneumobacillus, Yersinia, Acinetobacter, Legionella pneumophila, Bordetella pertussis*, and *Vibrio cholerae*.

3. The method for AST according to claim 1, wherein the antibiotic species includes at least one of cefazolin, cefepime, cefotetan, ceftazidime, ceftriaxone, ciprofloxacin, gentamicin, levofloxacin, nitrofurantoin, cotrimoxazole, amoxicillin or clarithromycin.

4. The method for AST according to claim 1, wherein in the temperature control unit, temperature is adjusted to a desired degree over the range of 32 degrees Fahrenheit to 158 degrees Fahrenheit, with a nonidentity of 32.9 degrees Fahrenheit.

* * * * *